United States Patent

Benda et al.

Patent Number: 5,501,807
Date of Patent: Mar. 26, 1996

[54] OVERBASED CARBOXYLATES

[76] Inventors: Rainer Benda, Avenue Salome 18, 1150-Brussels, Belgium; Edouard M. Mathieu, 10 Rue de la Mare Saint Aignan, 76130 Mont-Saint-Aignan; Olivier Letailleur, BB 32 Les Pommiers, 76170 Lillibone, both of France

[21] Appl. No.: 211,777

[22] Filed: Jul. 12, 1994

[30] Foreign Application Priority Data

Oct. 14, 1991 [GB] United Kingdom ............... 9121736.4

[51] Int. Cl.$^6$ ............................................. C10M 159/20
[52] U.S. Cl. ............................................. 252/18; 252/39
[58] Field of Search ............................................. 252/18, 39

[56] References Cited

U.S. PATENT DOCUMENTS

| | | | |
|---|---|---|---|
| 2,865,956 | 12/1958 | Rhuddlan et al. | 260/504 |
| 3,567,637 | 3/1971 | Sabol | 252/39 |
| 3,714,042 | 1/1973 | Greenough | 252/39 |
| 4,100,084 | 7/1978 | Powers, III | 252/39 |
| 4,824,585 | 4/1989 | Marotel et al. | 252/39 |
| 4,869,837 | 9/1989 | van Wijngaarden et al. | 252/39 |
| 4,938,882 | 7/1990 | Tipton | 252/39 |
| 5,281,345 | 1/1994 | Crawford et al. | 252/39 |

FOREIGN PATENT DOCUMENTS 298572  1/1989  European Pat. Off. .

*Primary Examiner*—Jerry D. Johnson
*Attorney, Agent, or Firm*—John J. Mahon; John F. Hunt; James A. Zboray

[57] ABSTRACT

High basicity calcium carboxylates useful as lubricant and fuel additives and in paints are obtained by carbonating a mixture of a $C_7$ to $C_{15}$ carboxylic preferably branched chain oxo-acid and excess calcium at from 15° to 60° C. in the presence of a volatile solvent. Products with a basicity of from 4 to 8 may be obtained.

6 Claims, No Drawings

OVERBASED CARBOXYLATES

The present invention relates to new calcium soaps possessing a high basicity, more commonly called overbased calcium soaps. Overbased additives have been extensively used in engine, gear and industrial lubricants as detergent inhibitors, extreme pressure and antiwear agents, anticorrosion and antirust additives. They can also be used as additives in fuels, as stabilizers in plastics, especially PVC, and in all sorts of anticorrosion coatings, including paints. The invention also relates to a method for preparing these overbased calcium soaps and to lubricants and fuels containing them.

The most widely known overbased calcium soaps are salts of alkylarylsulphonic acids. These are compounds which are difficult to prepare.

A traditional process for their preparation consists in reacting an alkylarylsulphonic acid with a metal oxide or hydroxide in a mineral oil. The reaction takes place in the presence of carbon dioxide ($CO_2$) and promoters which make the $CO_2$ easier to fix. The promoters are usually labile hydrogen compounds such as phenols, alcohols and aminoalcohols. When the reaction has ended, a cloudy solution (containing sediments) is obtained which is purified by centrifuging or filtration. Processes of this kind lead to calcium salts of alkylarylsulphonic acids which have a TBN (or Total Base Number) greater than or equal to 200, and capable of going up to 400 or higher. TBN is defined in ASTM standard D 2896-73.

In European Patent Application 0234149 basic calcium carboxylate soaps are described which do not possess the disadvantages of the known soaps and which have a basicity of up to 4 and yield perfectly stable and clear solutions in oil. Basicity is the total amount of calcium in the product divided by the amount of calcium linked to the carboxylic acid.

These products are made by carbonation of an excess of calcium hydroxide dispersed in a reaction medium containing an oil-soluble organic acid, a hydrocarbon solvent, a low molecular weight alcohol, and mineral oil, followed by filtration of the unreacted materials. Carbonation is carried out in the presence of catalysts such as metal oxides and zinc carboxylates and promoters such as higher alcohols, glycols, alkyl-phenols, or amines.

These products remain in the finished product and the presence of the catalyst and oil in the finished product can limit its use.

The object of the present invention is to prepare highly overbased products which can be used in many applications, through an improved process which can lead to products free of mineral oil, and catalysts.

The present invention therefore provides a process for the production of basic calcium carboxylic acid salts comprising i) Neutralising a $C_7$ to $C_{15}$ carboxylic acid in the presence of a volatile solvent ii) Adding excess calcium iii) Carbonating the mixture at a temperature of from 15° C. to 60° C.

iv) Removal of the volatile solvent and water and adding a diluent.

The reaction is generally carried out in the absence of carbonation catalysts.

The present invention further provides an overbased calcium carboxylic acid salt having a basicity from 4 to 8.

We prefer to use the carboxylic acids described in European Patent 0234149 preferably saturated $C_8$, $C_9$ and $C_{10}$ organic carboxylic acids which consist of isomeric mixtures and which are generally known as oxo acids. These oxo acids are characterized by a low linear acid content, generally less than or equal to 10% by weight, a low content of acids which are branched on carbon 2, generally less than or equal to 10% by weight, and a high content of acids which are mono- or polysubstituted on carbon 3 and/or carbons of higher rank, which is generally greater than 80% by weight. The oxo acids may be obtained by hydroformylation of $C_7$, $C_8$ and $C_9$ olefins, followed by an oxidation.

Among the organic carboxylic acids which are also suitable for the present invention there may also be added the derivatives which are mono- or polysubstituted in the 3-position and/or of higher rank of the acids corresponding to heptanoic acid, octanoic acid, nonanoic acid, decanoic acid, undecanoic acid and dodecanoic acid. These include, for example, 3-methylhexanoic acid, isooctanoic acid, 4,5-dimethylhexanoic acid, isononanoic acid, 3,5,5-trimethylhexanoic acid, isodecanoic acid, 3-ethyloctanoic acid, isoundecanoic acid, 4-ethylnonanoic acid and isododecanoic acid. The mixture of one or more of the above-mentioned acids, whether mixed or not with their isomers is also suitable for the present invention, it being preferred that the content of linear acids does not exceed 40% and that the content of acids which are substituted on carbon 2 does not exceed 20%. We have found that the linear acids and the acids branched on carbon 2 lead to the formation of a viscous product, or to the reaction mixture setting solid or, alternatively, to a precipitate which considerably limits the use of the product.

In a preferred embodiment of the process of the present invention calcium oxide and/or hydroxide is reacted with carbon dioxide and at least one organic carboxylic acid by passing the carbon dioxide through the reaction mixture. The process is characterized in that the reaction is performed in at least one organic solvent at a temperature of between 15° and 60° C., preferably 25° to 35° C. most preferably 27° to 30° C., and the acid is a saturated organic carboxylic acid containing from 7 to 15 carbon atoms, in which the content of linear acids is preferably less than or equal to 40% by weight, in which the content of acids branched on carbon 3 and/or the carbons of higher rank is equal to or higher than 40% by weight.

When the reaction has ended a diluent is generally added and the organic solvent and any water formed in the reaction may be removed by distillation. The product is usually filtered before or after removal of the organic solvent. The diluent may be oil or aromatic or aliphatic although an aliphatic diluent is preferred. Where the diluent is volatile it may subsequently be removed to yield a dry powdered product.

The volatile solvent preferably contains at least one nonpolar organic solvent chosen from naphtha, hexane, kerosene, benzene, toluene or xylene. It is also possible to use a mixture of paraffinic hydrocarbons of mineral or synthetic origin, preferably containing a low proportion of aromatic and/or naphthenic hydrocarbons, such as white spirit. It is preferred to also use polar organic cosolvents such as $C_1$ to $C_6$ alcohols, for example methanol, 1-butanol, 2-butanol, ethylene glycol, propylene glycol, ethylene glycol monomethyl ether, ethylene glycol dimethyl ether, diethylene glycol and its ethers, mixtures of alcohols derived from paraffin, methyl ethyl ketone, aromatic alcohols such as phenol; amines, for example aniline, phenylenediamine, or dodecylamine; or, yet again, a mixture of alcohols and/or amines, for example of methanol and aqueous ammonia. The preferred material is methanol, which gives the highest basicities and the shortest filtration times.

The molar ratio of calcium to the organic carboxylic acid employed in the reaction is generally between 2 and 4, which corresponds to a basicity of between 4 and 8. The period of carbonation is preferably between 1 and 6 hours, preferably 4 hours, such that the hourly mass ratio of carbon dioxide to calcium hydroxide is between 0.05 and 0.5, and more preferably between 0.1 and 0.2.

Where it is desired to use the products as oil additives their oil solubility may be improved by the addition of up to 50 wt %, preferably no more than 30 wt % based on the weight of carboxylic acid, of higher molecular weight organic acids to the reaction mixture. Examples of acids include monocarboxylic acids such as oleic or stearic acid and sulphonic acids such as alkyl aryl sulphonic acids. Preferred are the dicarboxylic acids such as the substituted succinic acids having the formula

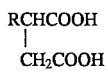

wherein R may be an olefin polymer-derived group formed by polymerization of such monomers as ethylene, propylene, 1-butene, isobutene, 1-pentene, 2-pentene, 1-hexene and 3-hexene. R may also be derived from a high molecular weight substantially saturated petroleum fraction.

The above-described classes of carboxylic acids derived from olefin polymers, and their derivatives, are well known in the art, and methods for their preparation as well as representative examples of the types useful in the present invention are described in detail in a number of U.S patents.

When dissolved in an oil, the calcium overbased soaps according to the invention can yield stable and completely clear solutions. In addition, they have a high TBN above 400, typically between 400 and 550. They find numerous applications, particularly as lubricant additives and in metal working fluids where they can impart detergent, extreme pressure, antiwear, anticorrosion and antirust properties. The metal working fluids may be straight oils, oil/water systems or totally aqueous. The calcium overbased salts may also be used as paint driers. Where the diluent is aliphatic it can be removed to produce diluent free powdered material useful as a paint additive.

The invention is illustrated by the following nonlimiting examples.

EXAMPLE 1

An overbased calcium $C_{8910}$ Cekanoic acid was prepared by the following steps.

A. Neutralisation of CEKANOIC 8910 acid with calcium hydroxide to produce neutral calcium carboxylate
   under vigorous stirring
   under cooling

| CHARGES | | | |
|---|---|---|---|
| | Parts by Weight | | |
| 1. Methanol | 240.00 | | raw material addition |
| 2. Toluene | 480.00 | | and |
| 3. Hydrated lime | 257.00 | | neutralisation/cooling |
| 4. Iso C8910 Acid | 208.00 | | (max temp 28° C.) |

As the neutralisation is exothermic, the C8910 acid is added at a low rate in order to keep the temperature below 28° C.

B. Carbonation to about 85% of stoechiometry and heat treatment to produce colloidally dispersed calcium carbonate and hydroxide.

Carbon dioxide 100.00 parts by weight
vigorous stirring
$CO_2$ sparging
28° C. for 4 hours.

The product which had a sediment content of about 3.0 volume % at the end of carbonation was heat soaked at from 28° to 60° C. for 1 hour and then at 60° C. for 15 minutes which reduced the sediment to 1 volume %.

C. Methanol/Water/Toluene Azeotrope Stripping
   in about 1.5 to 2 hours
   under NITROGEN sparging
   addition of anti-foam (droplets) as needed
   in order to decrease viscosity of the liquid phase 225.00 ml of Exxsol D100 diluent was added slowly after the stripping of the main quantity of methanol-water-toluene azeotrope.

D. Filtration

The product was filtered at ambient temperature at 5 bars pressure during the stripping after removal of 400 grams of the azeotrope when reaching 80° to 85° C.

35 grams of the filter aid were added.

| By-product | | |
|---|---|---|
| | Filter aid | 35 g |
| | Sediments | 25 g |
| | Diluted product | 23 g |
| Filtrate 1012.00 g | | 83 g filter cake |

E. Stripping to Recover the Remaining Process Solvents
   in about 1.5 to 2 hours
   under NITROGEN sparging
   under VACUUM (400 mmHG)
   maximum temperature 105° C.
   Product
   690.00 g of finished product were obtained having the following properties:

| Basicity | 4.94 |
|---|---|
| Calcium mass % | 15.7 |
| Kin.visco cst at 100° C. | 1033 |

EXAMPLES 2 to 17

The process of Example 1 was repeated using different acids and diluents. In Examples 13 and 14 the amount of hydrated lime used was increased to give a higher basicity. Examples 15 to 17 show the effect of using acids with different backbone structures. The properties of the products obtained are set out in the following table in which A.I means active ingredient and:

Varsol 110 is a desulphurised aliphatic hydrocarbon diluent boiling in the range 245° to 275° C., containing about 25% aromatics STANCO 150 is a solvent neutral naphthenic paraffinic oil PAO6 is a polyalpha olefin with kinematic viscosity of 6 centistrokes at 100° C.

EXXSOL D100 is a desulphurised, dearomatised hydrocarbon diluent

SA is $C_{24}$ alkyl benzene sulphonic acid

PIBSA is an alkenyl succinic anhydride in which the alkenyl group contains an average of 68 carbon atoms

| EXAMPLE | Acid + Diluent Used Mass % | | TBN | Basicity aspect | SOLUBILITY at 10% mass in STANCO 150/poly alpha olefin |
|---|---|---|---|---|---|
| | Iso Cekanoates C8, 9, 10 in Varsol 110 | | | | |
| 2 | iso C8, 9, 10 Varsol 110 | 100 110 | 480 | 3.5 clear liquid | STANCO 150: no |
| 3 | iso C8, 9, 10 Varsol 110 | 100 110 | 477 | 4.94 hazy liquid | STANCO 150: no |
| | Iso Cekanoates C8, 9, 10 in Exxsol D100 | | | | |
| 4 | iso C8, 9, 10 Pibsa in Exxsol D100 | 52 48 100 | 355 | 4,94 hazy liquid | STANCO 150: yes PA06: yes |
| 5 | iso C8, 9, 10 Pibsa in Exxsol D100 | 70 30 100 | 447 | 4.94 clear liquid | STANCO 150: no |
| 6 | iso C8, 9, 10 SA in Exxsol D100 | 55 45 100 | 428 | 4.94 liquid | STANCO 150: yes |
| 7 | iso C8, 9, 10 SA in Exxsol D100 | 77.5 22.5 100 | 500 | 4.94 liquid | STANCO 150: no |
| 8 | iso C8, 9, 10 Oleic acid in Exxsol D100 | 41.5 58.5 100 | 308 | 4.94 liquid/ gelling over time | STANCO 150: yes |
| | Iso Cekanoates C13 in Exxsol D100 | | | | |
| 9 | iso C13 in Essxol D100 | 100 100 | 512 | 4.94 hazy | STANCO 150: no |
| 10 | iso C13 Pibsa in Exxsol D100 | 80 20 100 | 481 | 4.94 hazy | STANCO 150: yes PA06: yes |
| 11 | iso C13 Oleic acid in Exxsol D100 | 80 20 100 | 512 | 4.94 hazy | STANCO 150: yes PA06: yes |
| 12 | iso C13 SA in Exxsol D100 | 80 20 100 | 452 | 4.94 | STANCO 150: yes PA06: yes |
| | Iso Cekanoates Ca mass % ratio increased | | | | |
| 13 | iso C8, 9, 10 in Exxsol D100 | 100 100 | 334 | 6.05 | STANCO 150: no tacky-translucent |
| 14 | iso C13 PIBSA in Exxsol D100 | 80 20 100 | 506 | 6.90 | STANCO 150: yes/ hazy |
| | Acid backbone structure | | | | |
| 15 | iso C9 in Exxsol D100 | 100 100 | 407 | 4.94 | |
| 16 | linear C9 in Exxsol D100 | 100 100 | paste | 4.94 | brittle paste tanslucent non tacky |
| 17 | neo C9, 10 in Exxsol D100 | 100 100 | paste | 4.94 | soft paste white |

When the diluent was removed from the product of Examples 8 to 12 and 14 a dry film was obtained which could readily be powdered.

Various of the Products were dissolved in a base lubricating oil (STANCO 150) and the oils subjected to the Four Ball Wear Test (ASTM D 4172) and the Four Ball Extreme Pressure Test (ASTM D 2783) and compared with the commercial product LZ 5347 available from Lubrizol. The results are in the table 2.

TABLE 2

ASTM D 2783 RESULTS

| PRODUCT OF EXAMPLE | LOAD WEAR INDEX | 4 BALL SEIZURE LOAD | EP WELD LOAD | % wt IN OIL |
|---|---|---|---|---|
| 11 | 35.1 | 100 KG | 160 KG | 3.9% |
| 14 | 43.6 | 126 KG | 160 KG | 3.9% |
| 4 | 45.6 | 100 KG | 126 KG | 5.6% |
| 12 | 43.1 | 126 KG | 160 KG | 4.4% |
| 10 | 45 | 126 KG | 200 KG | 4.2% |
| LZ 5347 | 37.6 | 100 KG | 200 KG | 5% |
| LZ 5347 | 47.8 | 126 KG | 250 KG | 10% |
| STANCO 150 | 26.5 | 80 KG | 126 KG | 0% |

ASTM D 4172 Results

The test was carried out for 60 minutes at a load of 50 kg at 75° C. at 1800 rotations per minute.

| PRODUCT OF EXAMPLE | WT % IN OIL | MINIMUM SCFP DIAMETER (mm) |
| --- | --- | --- |
| 11 | 3.9 | 1.905 |
| 4 | 5.6 | 1.87 |
| 12 | 4.4 | 0.39 |
| 10 | 4.2 | 0.355 |
| LZ 5347 | 5 | 0.34 |
| LZ 5347 | 10 | 0.39 |
| | 0 | 2.465 |

We claim:

1. A process for the production of basic calcium carboxylic acid salts comprising
   i) Neutralising a C7 to C15 aliphatic carboxylic acid in the presence of a volatile solvent
   ii) Adding excess calcium in which the molar ratio of calcium to the organic carboxylic acid is between 2 and 4
   iii) Carbonating the mixture at a temperature of from 15° C. to 60° C.
   iv) Removal of the volatile solvent and water of reaction and adding a diluent,
wherein the carboxylic acid comprises saturated C8, C9 and C10 oxo acids in which the oxo acids contains less than or equal to 10% by weight of linear acid, less than or equal to 10% by weight of acids which are branched on carbon 2, and greater than 80% by weight of acids which are mono- or polysubstituted on carbon 3 or carbons of higher rank, or C7 to C15 acids comprising acids mono- or polysubstituted in the 3-position or carbons of higher rank with less than 40% by weight of linear acids and less than 20% by weight of acids substituted on carbon 2.

2. A process according to claim 1 in which up to 50 wt % of a higher molecular weight organic acid is added to the reaction mixture.

3. A process according to claim 1 in which the volatile solvent contains at least one non polar organic solvent chosen from naptha, hexane, kerosene, benzene, toluene or xylene.

4. A process according to claim 3 in which the volatile solvent also contains organic cosolvents chosen from $C_1$ to $C_6$ alcohols.

5. A process according to claim 1 including the additional step of removing the diluent.

6. A process according to claim 3 in which the volatile solvent also contains organic cosolvents chosen from the group consisting of methanol, 1-butanol, 2-butanol, ethylene glycol, propylene glycol, ethylene glycol monomethyl ether, ethylene glycol dimethyl ether and diethylene glycol.

* * * * *